United States Patent
Kim et al.

(10) Patent No.: US 12,029,493 B2
(45) Date of Patent: Jul. 9, 2024

(54) ORTHOGNATHIC SYSTEM USING THREE-DIMENSIONAL HYBRID IMAGE BUILDING PROGRAM

(71) Applicants: MEGAGEN IMPLANT CO., LTD., Gyeongsan-si (KR); Jong Cheol Kim, Daegu (KR)

(72) Inventors: Jong Cheol Kim, Daegu (KR); Kwang Bum Park, Daegu (KR)

(73) Assignees: MEGAGEN IMPLANT CO., LTD. (KR); Jong Cheol Kim (KR)

( * ) Notice: Subject to any disclaimer, the term of this patent is extended or adjusted under 35 U.S.C. 154(b) by 1009 days.

(21) Appl. No.: 16/492,607

(22) PCT Filed: Feb. 19, 2018

(86) PCT No.: PCT/KR2018/001996
§ 371 (c)(1),
(2) Date: Sep. 9, 2019

(87) PCT Pub. No.: WO2018/164391
PCT Pub. Date: Sep. 13, 2018

(65) Prior Publication Data
US 2021/0137599 A1 May 13, 2021

(30) Foreign Application Priority Data
Mar. 7, 2017 (KR) .......................... 10-2017-0029005

(51) Int. Cl.
*A61B 34/10* (2016.01)
*A61B 6/00* (2006.01)
(Continued)

(52) U.S. Cl.
CPC .............. *A61B 34/10* (2016.02); *A61B 6/032* (2013.01); *A61B 6/505* (2013.01); *A61B 6/51* (2024.01);
(Continued)

(58) Field of Classification Search
CPC ............ A61B 34/10; A61B 6/032; A61B 6/14; A61B 6/505; A61B 6/5223; A61B 6/563;
(Continued)

(56) References Cited

U.S. PATENT DOCUMENTS

| 8,170,327 | B2* | 5/2012 | Glor | .................. A61C 13/0004 |
| | | | | 382/154 |
| 10,448,956 | B2* | 10/2019 | Gordon | .................. A61B 17/15 |
| 2004/0015327 | A1* | 1/2004 | Sachdeva | .................. A61C 7/00 |
| | | | | 702/167 |

FOREIGN PATENT DOCUMENTS

| CN | 104771231 A | 7/2015 |
| JP | 2007037687 A | 2/2007 |

(Continued)

*Primary Examiner* — Peter Luong
(74) *Attorney, Agent, or Firm* — Renaissance IP Law Group LLP

(57) ABSTRACT

An orthognathic system using a 3-dimensional hybrid image constructing program according to an embodiment of the present invention includes: a dental clinic server configured to prepare preliminary data for orthognathic surgery based on CT image data acquired by a CT imaging apparatus, transmit the preliminary data to an orthognathic device manufacturer server, perform virtual orthognathic surgery by inputting osteotomy data received from the orthognathic device manufacturer server into the 3-dimensional hybrid image constructing program, and transmit the result of the virtual orthognathic surgery to the orthognathic device manufacturer server; and an orthognathic device manufacturer server configured to merge CT data with gingival data, extract this to generate a jaw-bone 3-dimensional image file, cut the jaw bones within the program by using the generated jaw-bone 3-dimensional image file, and transmit the data to the dental clinic server.

8 Claims, 12 Drawing Sheets

(51) Int. Cl.
- *A61B 6/03* (2006.01)
- *A61B 6/50* (2024.01)
- *A61B 6/51* (2024.01)
- *A61B 17/15* (2006.01)
- *A61B 17/80* (2006.01)
- *A61B 17/84* (2006.01)
- *A61C 9/00* (2006.01)
- *A61C 13/00* (2006.01)
- *G16H 20/40* (2018.01)
- *G16H 30/40* (2018.01)
- *G16H 50/20* (2018.01)
- *G16H 50/50* (2018.01)

(52) U.S. Cl.
CPC ............ *A61B 6/5223* (2013.01); *A61B 6/563* (2013.01); *A61B 17/151* (2013.01); *A61B 17/8071* (2013.01); *A61B 17/846* (2013.01); *A61C 9/0006* (2013.01); *A61C 13/0004* (2013.01); *G16H 20/40* (2018.01); *G16H 30/40* (2018.01); *G16H 50/20* (2018.01); *G16H 50/50* (2018.01); *A61B 2034/104* (2016.02); *A61B 2034/105* (2016.02); *A61B 2034/108* (2016.02)

(58) Field of Classification Search
CPC . A61B 17/151; A61B 17/8071; A61B 17/846; A61B 17/68; A61B 2034/104; A61B 2034/105; A61B 2034/108; A61B 2034/102; A61B 2090/365; A61B 2090/367; A61B 90/40; A61C 9/0006; A61C 9/0053; A61C 13/0004; A61C 7/002; A61C 8/00; A61C 8/0089; G16H 20/40; G16H 30/40; G16H 50/20; G16H 50/50; G06T 2207/30052

See application file for complete search history.

(56) References Cited

FOREIGN PATENT DOCUMENTS

| | | |
|---|---|---|
| KR | 20120132647 A | 12/2012 |
| KR | 20130044934 A | 5/2013 |
| KR | 20160143368 A | 12/2016 |
| KR | 101706334 B1 | 2/2017 |

* cited by examiner (A)             (B)

(A)

(B)

(A)          (B)

(A)           (B)

ORTHOGNATHIC SYSTEM USING THREE-DIMENSIONAL HYBRID IMAGE BUILDING PROGRAM

TECHNICAL FIELD

The present invention relates generally to an orthognathic system and, more particularly, to an orthognathic system using a 3-dimensional hybrid image constructing program that converts the CBCT data of a patient into a 3-dimensional image file and merges the scan data of a working model into the converted image to construct a precise 3-dimensional image.

BACKGROUND ART

Orthognathic surgery (corrective jaw surgery, jaw surgery) refers to surgery designed to correct abnormalities in the form or shape of the maxilla or mandible when the growth of the maxilla or mandible has resulted in overdevelopment, underdevelopment, or an asymmetrical state beyond what is normal. Since orthognathic surgery brings about positional changes in the jaw bones, an orthodontic treatment is generally applied before and after the surgery. The planning for the surgery typically entails collaboration between an orthodontist and the oral maxillofacial surgeon. Thus, compared to regular surgery, the surgery entails a longer overall period and a more complicated set of procedures, due to the inclusion of preparation steps and post-surgery occlusal treatments, etc.

In the field of orthognathic procedures, methods of utilizing guides based on 3D simulations are being introduced. Most of these methods, however, are limited to recreating the jaw bone relationship using the occlusal relationship of the maxillary and mandibular teeth. While the major steps of orthognathic surgery include diagnosis, jaw bone separation, and fixation, the above methods provide results only for the final step, i.e. fixation, and do not provide sufficient preparation for the potentially more dangerous step of jaw bone separation. Also, since there are no objective indices regarding the proper movement of the jaw bone after the osteotomy, the procedure relies entirely on the discretion of the surgeon.

Korean Patent Application Publication No. 10-2013-0008236 (Patent Document 1) discloses an "Image matching data creation method for orthognathic surgery and method for the orthognathic simulation surgery using the same", which involve removing noise from a CT (computed tomography) image of the patient's facial bone, improving accuracy at the maxillary and mandibular teeth area using 3-dimensional scan data of the teeth area, and including occlusion information using such image information, to enable accurate orthognathic simulation surgery.

Also, Korean Patent Application Publication No. 10-2013-0075305 (Patent Document 2) discloses a "Simulation Method, Recorder and Apparatus for Orthognathic Surgery", which involve scanning a maxilla model, a mandible model, and a maxilla/mandible model in a centric occlusion state assembled using a real model obtained via dental impressions taken from the patient's oral cavity, generating a centric-occlusion digital dental model by assembling the scanned images, separating a model that includes at least one of soft tissue, bone, teeth, a corrective bracket, and a surgical hook from the CT image of the patient, processing each of the models and the centric-occlusion digital dental model into 3-dimensional images, and overlapping the maxilla/mandible model, corrective bracket, and surgical hook separated from the CT image over the palatal soft tissue, so as to accurately display the occlusal relationship after the procedure or correction and to enable an easier manufacture of a surgical splint.

The technologies disclosed in Patent Documents 1 and 2 above both relate to orthognathic surgery and provide the advantages of allowing accurate orthognathic simulation surgery or accurately displaying the occlusal relationship after the procedure or correction.

However, the related art is limited to orthodontics associated with orthognathic surgery or is limited in terms of the relationship between simulation surgery and actual surgery, and there is an overall insufficiency in preparations regarding the jaw bone separation process.

DETAILED DESCRIPTION OF THE INVENTIVE CONCEPT

Technical Problem

Accordingly, the present invention has been made keeping in mind the above problems occurring in the related art, and the present invention is intended to provide an orthognathic system using a 3-dimensional hybrid image constructing program that enables safe and efficient orthognathic surgery by converting CBCT (cone beam computed tomography) data of a patient into a 3-dimensional image file, merges the scan data of a model of the oral cavity and jaw bones into the converted image to construct a precise 3-dimensional hybrid image, and allows the operator to perform virtual orthognathic surgery and manufacture an orthognathic assist device needed for actual orthognathic surgery.

In order to achieve the objective above, according to one aspect of the present invention, there is provided an orthognathic system using a 3-dimensional hybrid image constructing program, wherein the orthognathic system includes a CT imaging apparatus, a dental clinic server, and an orthognathic device manufacturer server and is configured to perform actual orthognathic surgery based on a preparatory action for orthognathic surgery that is performed based on an exchange of a series of data associated with orthognathic surgery between the dental clinic server and the orthognathic device manufacturer server.

The orthognathic system includes: a CT imaging apparatus configured to perform a CT imaging of a skull of a patient receiving orthognathic surgery for orthognathic diagnosis planning;

a dental clinic server configured to prepare preliminary data for orthognathic surgery based on CT image data acquired by the CT imaging apparatus, transmit the preliminary data to the orthognathic device manufacturer server, perform virtual orthognathic surgery by inputting osteotomy data received from the orthognathic device manufacturer server into the 3-dimensional hybrid image constructing program, and transmit a result of the virtual orthognathic surgery to the orthognathic device manufacturer server; and an orthognathic device manufacturer server configured to merge CT data with gingival data based on the preliminary data received from the dental clinic server by using the 3-dimensional hybrid image constructing program, extract this to generate a jaw-bone 3-dimensional image file for virtual orthognathic surgery, cut the jaw bone within a program by using the generated jaw-bone 3-dimensional image file, and transmit the data relevant to the osteotomy to the dental clinic server.

Here, a scanner configured to scan an oral-cavity model fabricated by way of a dental impression taken from the patient receiving orthognathic surgery may further be included.

Also, the preliminary data prepared may be obtained by incorporating oral-cavity model scan data, obtained by scanning the oral-cavity model, into the CT image of the skull of the patient.

Also, the 3-dimensional hybrid image constructing program may include a dental implant module or an orthognathic surgery module.

Here, the dental implant module may implement an environment for implant diagnosis and virtual diagnosis by overlapping the CT data of the patient and a 3D scanned image of the oral cavity or an oral-cavity model.

Also, the dental implant module may choose an implanting position, by merging an image of the repaired tooth onto the data obtained after overlapping the CT data and the 3D scanned image of the oral cavity or the oral-cavity model, and may determine the orthognathic surgery method and the drilling order, etc. for the implanting by using a color bone quality analysis of the implanting site.

Also, the orthognathic surgery module may analyze the jaw bone in a 3D model, present an orthognathic surgery method suitable for the patient, cut the necessary parts in the 3D model accordingly, perform the virtual orthognathic surgery, and recreate the positional relationship of the jaw bone altered after the orthognathic surgery.

Also, the orthognathic surgery module may be configured to design the sawing guides, needed for cutting the jaw bones, and fixation plates, for affixing and accurately recreating the positional relationship of the jaw bone, based on the recreated result.

Here, holes for affixing the sawing guide and holes for affixing the fixation plate may be designed such that at least one pair of holes are formed in the same position.

Also, the orthognathic device manufacturer server may be configured to perform a surface treatment on 3-dimensional image data (image) for precise virtual orthognathic surgery prior to cutting the jaw bone in the program.

Also, the dental clinic server, in performing the virtual orthognathic surgery, may move and rotate jaw bone pieces that have been cut into separated parts within the program to perform the virtual orthognathic surgery.

Also, the orthognathic device manufacturer server may further be configured to compare the result of the virtual orthognathic surgery received from the dental clinic server with the CT analysis data from before the orthognathic surgery to verify whether or not the result of the virtual orthognathic surgery is adequate.

Also, the orthognathic device manufacturer server may further be configured to design an orthognathic assist device based on the result of the virtual orthognathic surgery received from the dental clinic server.

Here, the orthognathic assist device may include a sawing guide for cutting each jaw bone during the actual orthognathic surgery, a jaw-bone fixation plate for guiding the position of a fixation pin that affixes the jaw bone after each part of the jaw bone cut by way of the sawing guide is moved by the virtual orthognathic surgery, and an arch securing plate (intermittent stent) serving as a temporary fixture clamped between the maxilla and the mandible for securing the maxillary arch and mandibular arch onto positions of the virtual orthognathic surgery when affixing the jaw-bone fixation plate.

Advantageous Effects

An embodiment of the invention may thus utilize a 3-dimensional image constructing program to enable virtual orthognathic surgery, based on the result of which an orthognathic assist device needed for actual orthognathic surgery may be designed, manufactured, and provided to the orthognathic operator, so that the orthognathic operator may perform an orthognathic procedure on the patient in a safe and efficient manner with minimal surgical side effects.

MODE OF THE INVENTIVE CONCEPT

The terms or words used in the specification and claims are not to be limited in interpretation to common or dictionary meanings and should be interpreted to convey the meanings and concepts that are in harmony with the technical spirit of the present invention, in accordance with the principle that the inventor may suitably define the concept of a term to best describe the invention.

Throughout the specification, reference to a part "including" or "comprising" an element does not preclude the existence of one or more other elements and reserves the possibility of there being one or more other elements unless specifically stated otherwise. Also, a term such as "part", "device", "module", "apparatus", etc. used in the specification may refer to a unit that performs at least one function or action, where the unit may be implemented in hardware or software form or as a combination of hardware and software.

Certain embodiments of the present invention are described below in more detail with reference to the accompanying drawings.

Figure 1:
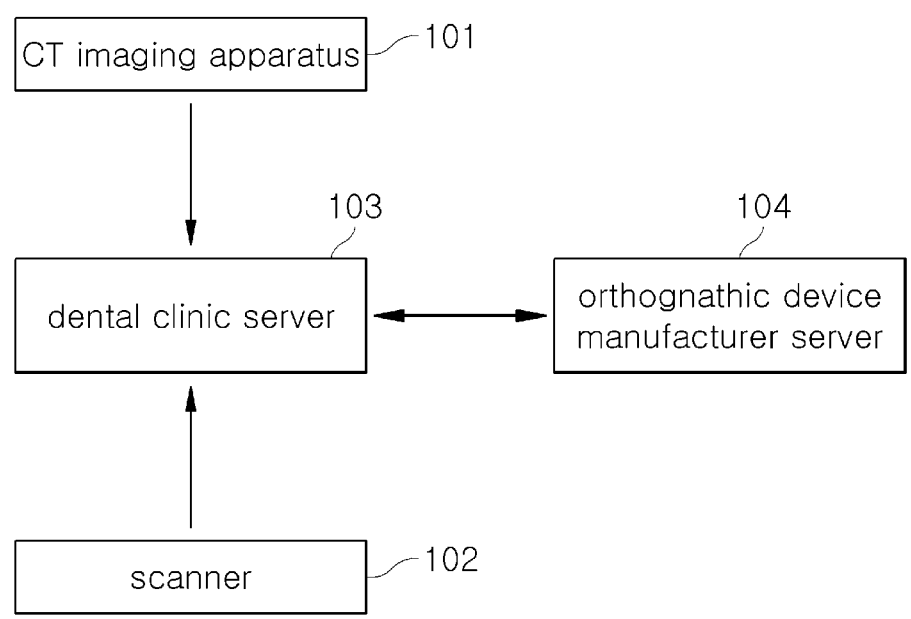
FIG. 1 is a diagram conceptually illustrating the composition of an orthognathic system using a 3-dimensional hybrid image constructing program according to an embodiment of the present invention.

FIG. 1 is a diagram conceptually illustrating the composition of an orthognathic system using a 3-dimensional hybrid image constructing program according to an embodiment of the present invention.

Referring to FIG. 1, an orthognathic system 100 using a 3-dimensional hybrid image constructing program according to an embodiment of the present invention is an orthognathic system that includes a CT imaging apparatus 101, a dental clinic server 103, and an orthognathic device manufacturer server 104. After the dental clinic server and the orthognathic device manufacturer server perform preparatory actions for orthognathic surgery through a series of exchanges of orthognathic surgery-related data, the orthognathic system may perform actual orthognathic surgery based on the preparatory actions. Here, an orthognathic system 100 based on the present invention can further include a scanner 102, as shown in the drawing.

The CT imaging apparatus 101 takes CT images of the skull of the patient receiving orthognathic surgery to establish an orthognathic diagnosis plan.

The scanner 102 scans an oral-cavity model fabricated by way of dental impressions taken from the patient receiving orthognathic surgery. Here, the oral-cavity model may be fabricated by a dentist or by an orthognathic device manufacturer. Also, the scanner 102 does not necessarily have to be a part of the orthognathic system and may be omitted from the orthognathic system in some cases. That is, if the CT imaging apparatus 101 is equipped with a function for scanning the oral-cavity model or the actual oral cavity of the patient receiving orthognathic surgery, then the scanner 102 may be omitted. For the sake of convenience, this embodiment is described using an example in which a separate scanner 102 is included in the orthognathic system.

The dental clinic server 103 prepares preliminary data for orthognathic surgery based on the CT image data taken by the CT imaging apparatus 101 and the scan data obtained by the scanner 102 and transmits the preliminary data to the orthognathic device manufacturer server 104, inputs osteotomy data received from the orthognathic device manufacturer server 104 into the 3-dimensional hybrid image constructing program to perform virtual orthognathic surgery, and transmits the result of the virtual orthognathic surgery to the orthognathic device manufacturer server 104. Here, in performing the virtual orthognathic surgery, the dental clinic server 103 may move and rotate the jaw bone pieces cut into separated parts in the program to perform the virtual orthognathic surgery.

Also, the preliminary data prepared by the dental clinic server 103 as above may be obtained by merging the oral-cavity model scan data, obtained by scanning the oral-cavity model, onto the CT image of the patient's skull. Also, the 3-dimensional hybrid image constructing program may include a dental implant module or an orthognathic surgery module. Here, the dental implant module may implement an environment for implant diagnosis and virtual diagnosis by overlapping the CT data of the patient with a 3D scanned image of the oral cavity or the oral-cavity model.

Also, the implant module may choose an implanting position, by merging an image of the repaired tooth onto the data obtained after overlapping the CT data and the scanned image of the oral cavity or the oral-cavity model, and may determine the orthognathic surgery method and the drilling order for implanting, etc. by using a color bone quality analysis of the implanting site.

Also, the orthognathic surgery module may analyze the jaw bone within a 3D model, present an orthognathic surgery method suitable for the patient, cut the necessary parts in the 3D model accordingly, perform the virtual orthognathic surgery, and then recreate the positional relationship of the jaw bone altered after the orthognathic surgery.

Also, the orthognathic surgery module may include a function for designing the sawing guides needed for cutting the jaw bone and the fixation plates for affixing the jaw bones and accurately recreating the positional relationship based on the recreated result. Here, holes for affixing the sawing guides and holes for affixing the fixation plate may be designed such that at least one pair of holes are formed in the same position.

The orthognathic device manufacturer server 104 merges the CT data with gingival data based on the preliminary data received from the dental clinic server 103 by using the 3-dimensional hybrid image constructing program, extracts this to generate a jaw-bone 3-dimensional image file for virtual orthognathic surgery, cuts the jaw bones within the program by using the generated jaw-bone 3-dimensional image file, and transmits the data to the dental clinic server 103. Here, the orthognathic device manufacturer server 104 may be equipped with a function for performing a surface treatment on the 3-dimensional image data (image) for precise virtual orthognathic surgery prior to cutting the jaw bones in the program.

Also, the orthognathic device manufacturer server 104 may further include a function for comparing the result of the virtual orthognathic surgery received from the dental clinic server 103 with the CT analysis data from before the orthognathic surgery to verify whether or not the result of the virtual orthognathic surgery is adequate.

Also, the orthognathic device manufacturer server 104 may further include a function for designing an orthognathic assist device based on the result of the virtual orthognathic surgery received from the dental clinic server 103. Here, while it is possible to have the orthognathic assist device designed at the orthognathic device manufacturer end, it is also possible to have the orthognathic assist device designed at a professional design company. That is, the design and manufacture of the orthognathic assist device may be performed by different companies.

Here, the orthognathic assist device may include sawing guides for cutting the jaw bones during actual orthognathic surgery, jaw-bone fixation plates for guiding the position of fixation pins that affix the jaw bones after the parts of the jaw bones cut by way of the sawing guides are moved by the virtual orthognathic surgery, and an arch securing plate (intermittent stent) serving as a temporary fixture clamped between the maxilla and the mandible to secure the maxillary arch and mandibular arch onto positions of the virtual orthognathic surgery when affixing the jaw-bone fixation plate. A further description of the orthognathic assist device will be provided later on.

Below, a description is provided of a process for performing orthognathic surgery with an orthognathic system using a 3-dimensional hybrid image constructing program according to an embodiment of the present invention structured as above.

Figure 2:
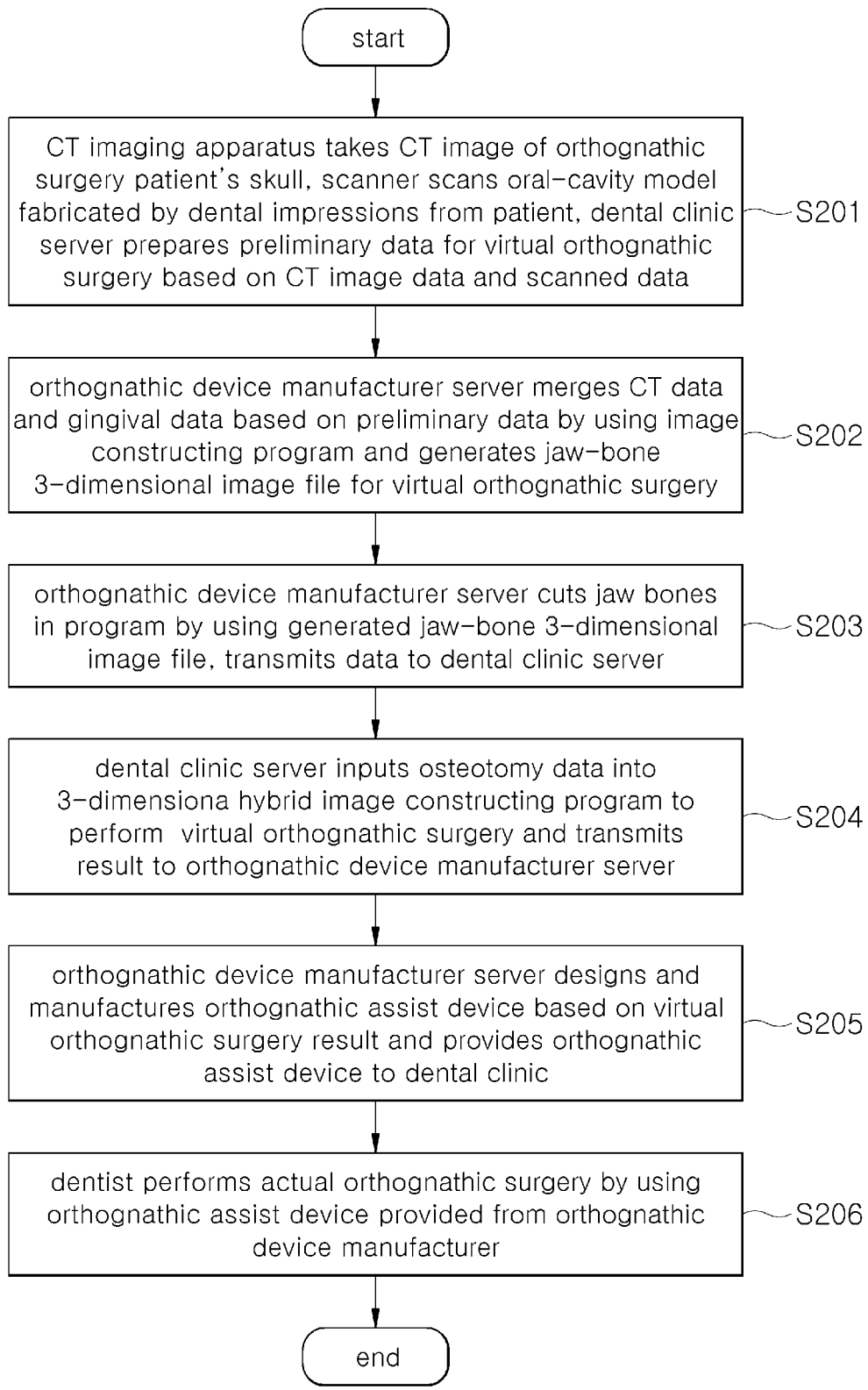
FIG. 2 is a flow diagram illustrating the process of an orthognathic operation based on an orthognathic system using a 3-dimensional hybrid image constructing program according to an embodiment of the present invention.

FIG. 2 is a flow diagram illustrating the process of an orthognathic operation based on an orthognathic system using a 3-dimensional hybrid image constructing program according to an embodiment of the present invention.

Referring to FIG. 2, an orthognathic system 100 using a 3-dimensional hybrid image constructing program according to an embodiment of the present invention is, as described above, an orthognathic system that includes a CT imaging apparatus 101, a scanner 102, a dental clinic server 103, and an orthognathic device manufacturer server 104 and performs actual orthognathic surgery based on preparatory actions for orthognathic surgery conducted through a series of exchanges of orthognathic surgery-related data between the dental clinic server 103 and the orthognathic device manufacturer server 104. First, to establish an orthognathic diagnosis plan, the CT imaging apparatus 101 takes a CT image of the skull of the patient receiving the orthognathic surgery, the scanner 102 scans an oral-cavity model fabricated via dental impressions taken from the patient, and the dental clinic server 103 prepares preliminary data for virtual orthognathic surgery based on the CT image data obtained from the CT imaging and the scan data obtained by the scanning and transmits the preliminary data to the orthognathic device manufacturer server 104 (step S201). Here, the preliminary data may be obtained by merging the oral-cavity model scan data, which is obtained by scanning the oral-cavity model, onto the CT image of the patient's skull by using diagnosis software (i.e. the 3-dimensional hybrid image constructing program described later on). Here, the reason for fabricating the oral-cavity model from dental impressions taken of the patient and scanning the oral-cavity model as above is to compensate portions of the CT image made unclear by diffuse reflection from metal teeth or metal dental prostheses which the patient may have, as well as to accurately identify the occlusion of the patient during the virtual orthognathic surgery.

Figure 3:
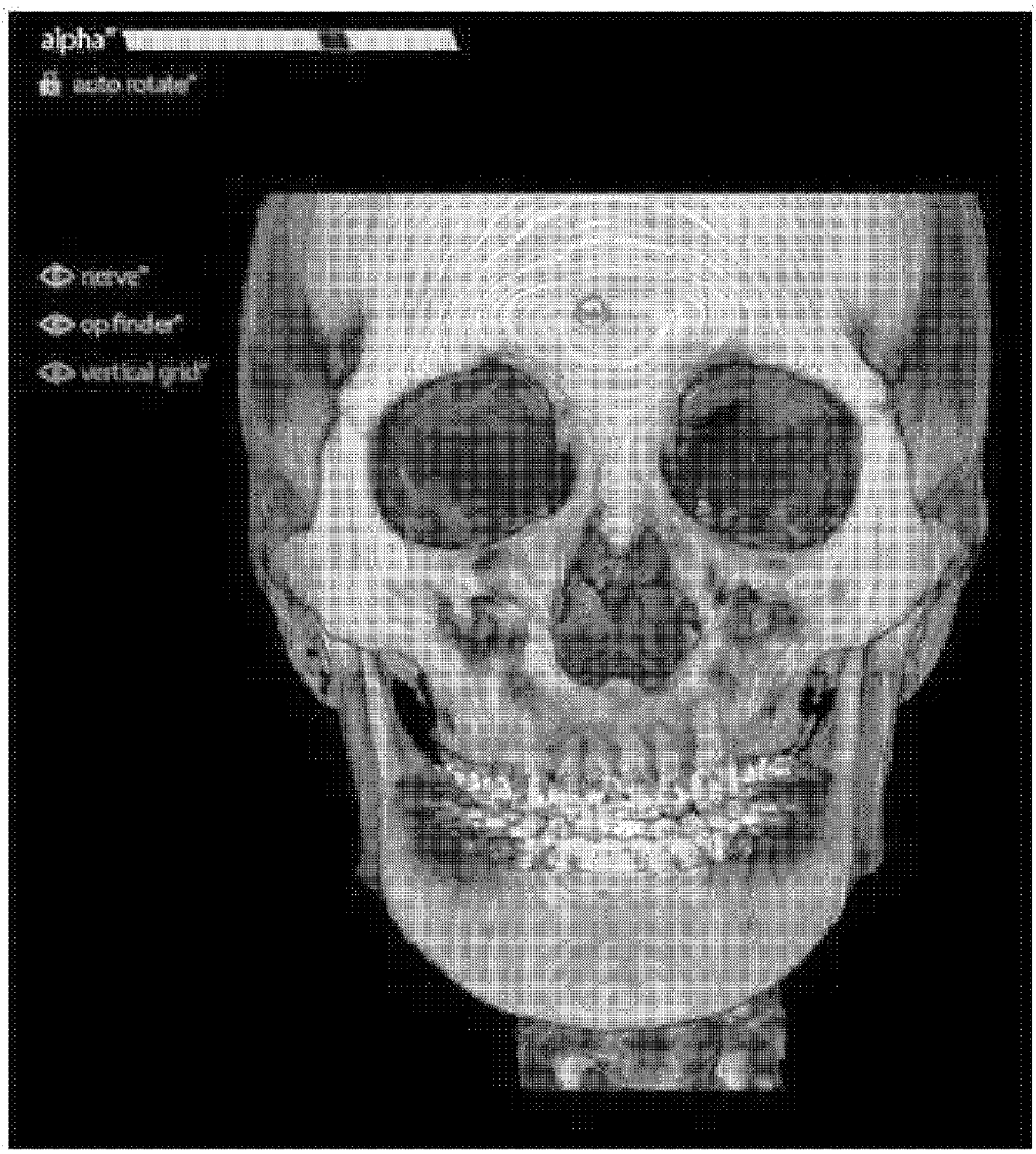
FIG. 3 shows a CT scan image of the skull of a patient receiving orthognathic surgery by way of an orthognathic system according to an embodiment of the present invention.
Figure 4:
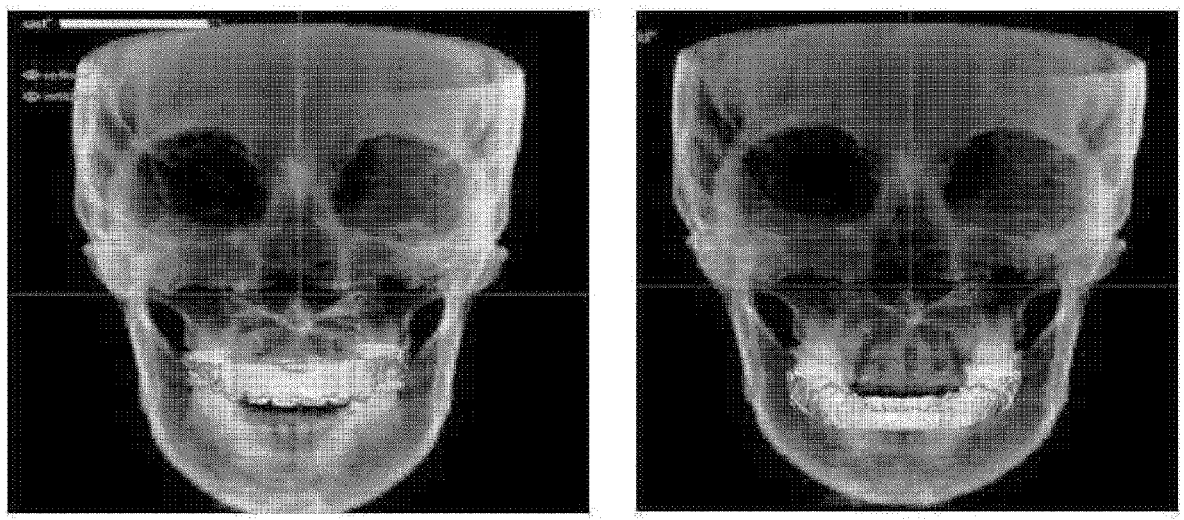
FIG. 4 shows oral-cavity model scan data merged onto a CT image for diffuse reflection compensation using an orthognathic system according to an embodiment of the present invention.

FIG. 3 shows a CT scan image of the skull of a patient receiving orthognathic surgery, and FIG. 4 shows oral-cavity model scan data merged onto a CT image for diffuse reflection.

Figure 5:
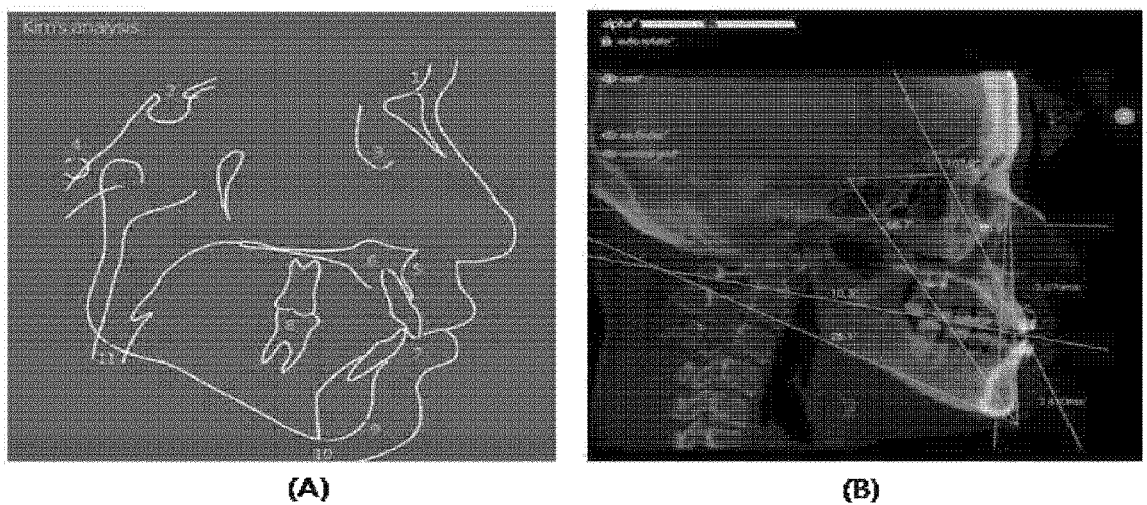
FIG. 5 shows images associated with designating major measurement points on the facial bone and analyzing the facial structure based on CT data using an orthognathic system according to an embodiment of the present invention.

Also, the dental clinic server 103 designates major measurement points of the facial bone for CT data analysis as in drawing (A) of FIG. 5, uses CT data to analyze the facial structure of the patient with respect to the designated points as in drawing (B), and plans the required amount of movement and amount of removal for the maxilla and mandible according to the analysis result.

Next, based on the preliminary data received from the dental clinic server 103, the orthognathic device manufacturer server 104 merges the CT data and gingival data by using the 3-dimensional hybrid image constructing program and extracts this to generate a jaw-bone 3-dimensional image file for virtual orthognathic surgery (step S202). Here, the merging of the CT data and gingival data based on preliminary data by using the 3-dimensional hybrid image constructing program and the generating of the jaw-bone 3-dimensional image file for the virtual orthognathic surgery need not be limited to being performed by the orthognathic device manufacturer server 104 and, in some cases, may be performed by the dental clinic server 103.

Figure 6:
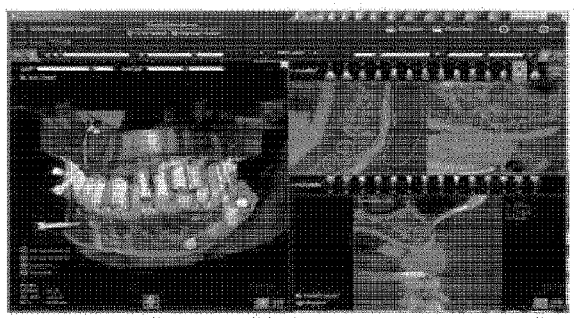
FIG. 6 shows an implant module and an orthognathic surgery module in a 3-dimensional hybrid image constructing program employed by an orthognathic system according to an embodiment of the present invention.
Figure 6:
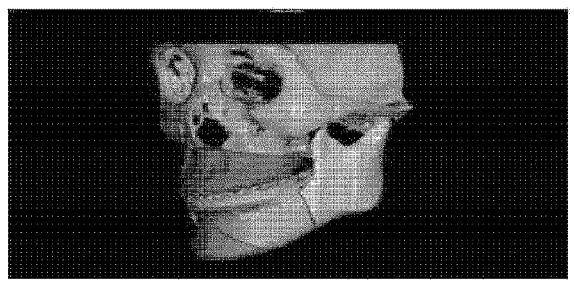

As illustrated in FIG. 6, the 3-dimensional hybrid image constructing program includes a dental implant module (A) or an orthognathic surgery module (B).

Here, the dental implant module (A) implements an environment for implant diagnosis and virtual diagnosis by overlapping the CT data of the patient and a 3D scanned image of the oral cavity or the oral-cavity model, as described above. The dental implant module (A) chooses the optimal implanting position, by merging an image of a repaired tooth onto the data obtained after overlapping the CT data and the 3D scanned image of the oral cavity or the oral-cavity model, and determines the orthognathic surgery method and the drilling order, etc. for the implanting by using a color bone quality analysis of the implanting site.

Also, the orthognathic surgery module (B) analyzes the jaw bones in a 3D model, presents an orthognathic surgery method suitable for the patient, cuts the necessary parts in the 3D model accordingly, and performs the virtual orthognathic surgery, to recreate the positional relationship of the jaw bones altered after the orthognathic surgery. Based on the recreated result, the orthognathic surgery module (B) designs the sawing guides needed for cutting the jaw bones and the fixation plates for affixing and accurately recreating the positional relationship of the jaw bones. Here, the holes for affixing the sawing guides and holes for affixing the fixation plates may be designed such that at least one pair of holes are formed in the same position, as described above.

Figure 7:
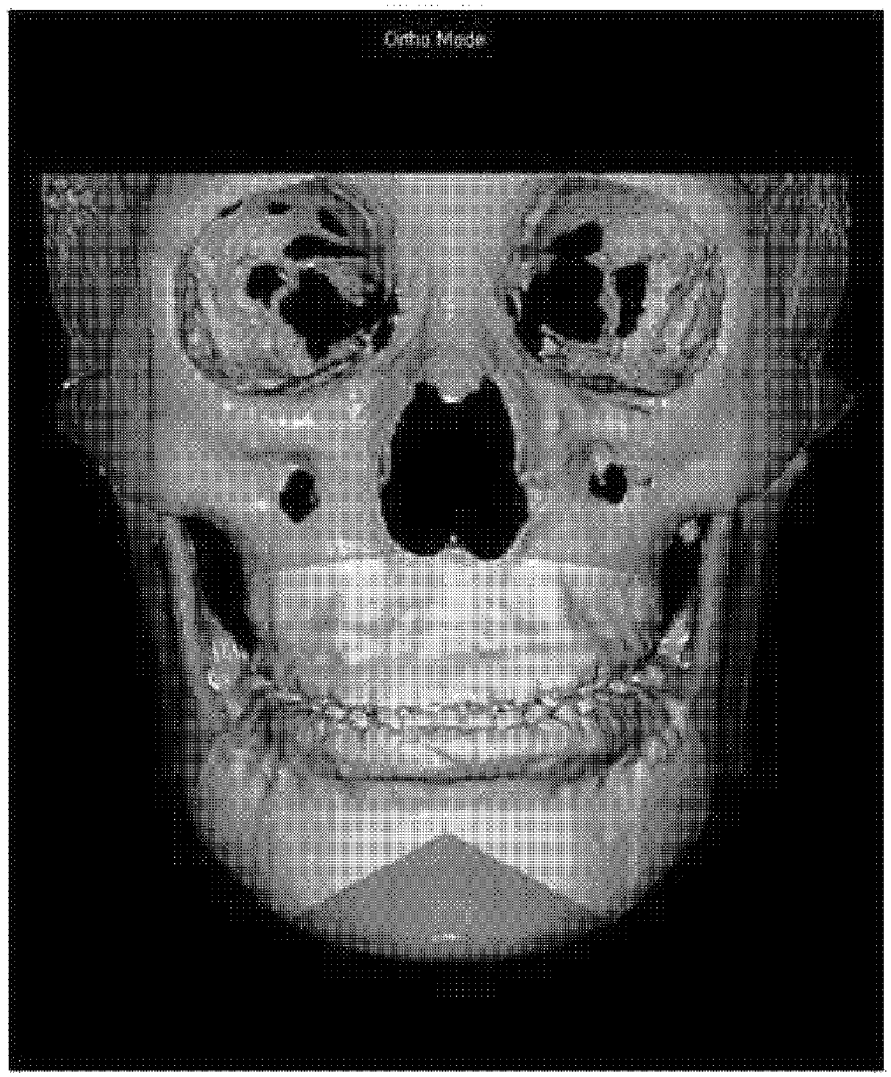
FIG. 7 shows a jaw-bone 3-dimensional image file that has been generated and applied with a surface treatment using an orthognathic system according to an embodiment of the present invention.

After the orthognathic device manufacturer server generates a jaw-bone 3-dimensional image file for virtual orthognathic surgery as above, the orthognathic device manufacturer server 104 cuts the jaw bones within the program by using the generated jaw-bone 3-dimensional image file, and transmits the data to the dental clinic server 103 (step S203). Here, before cutting the jaw bones in the program, a surface treatment may be applied to the 3-dimensional image data (image), as in FIG. 7, for greater precision in the virtual orthognathic surgery. Also, cutting the jaw bones within the program may be performed by a typical osteotomy method for orthognathic surgery, as in FIG. 8.

Afterwards, the dental clinic server 103 inputs the osteotomy data received from the orthognathic device manufacturer server 104 into the 3-dimensional hybrid image constructing program to perform virtual orthognathic surgery and transmits the result to the orthognathic device manufacturer server 104 (step S204). Here, the virtual orthognathic surgery is performed by moving and rotating the jaw bone pieces cut into separate parts within the program to perform the virtual orthognathic surgery.

Figure 8:
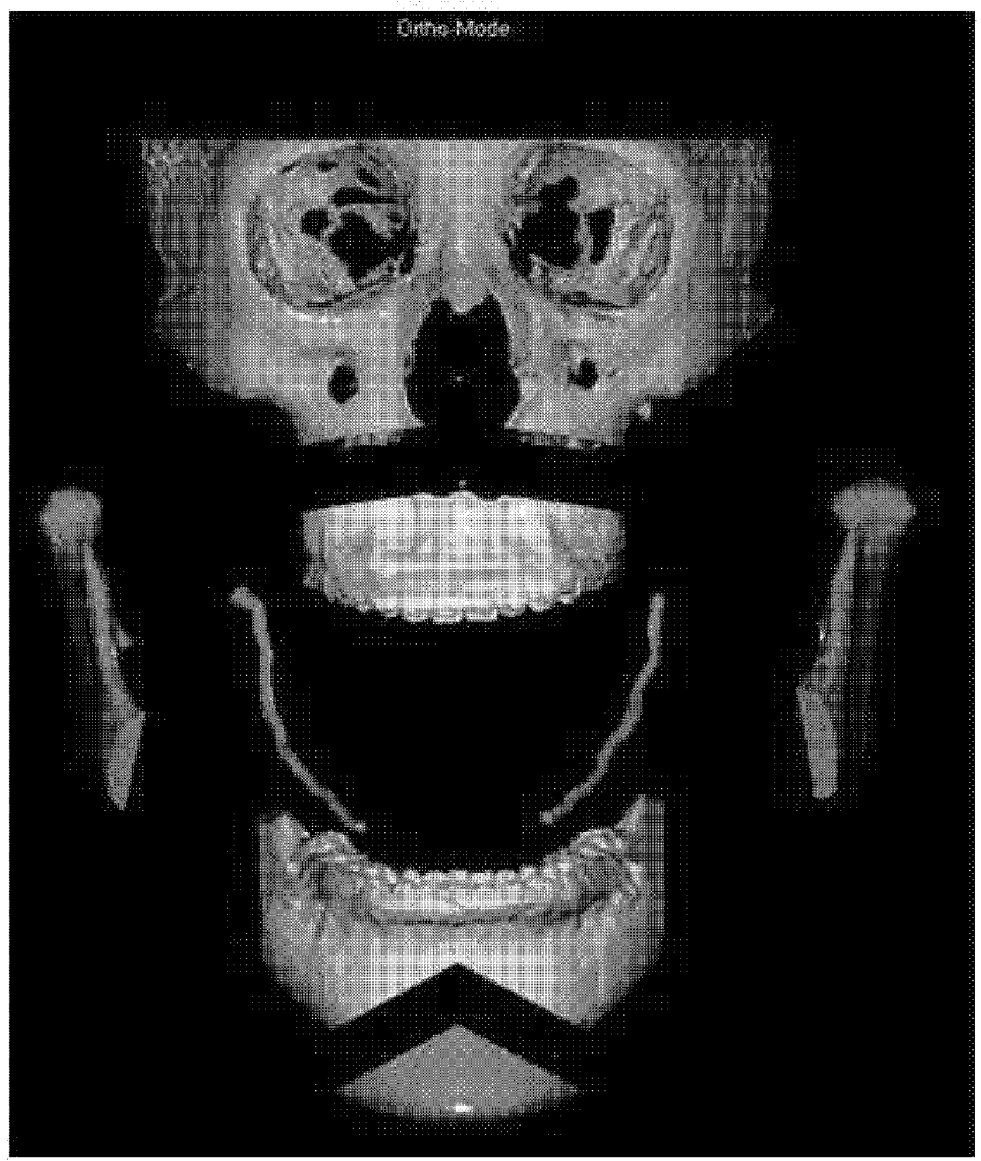
FIG. 8 shows the jaw bones cut in accordance to a typical osteotomy method for orthognathic surgery using an orthognathic system according to an embodiment of the present invention.
Figure 9:
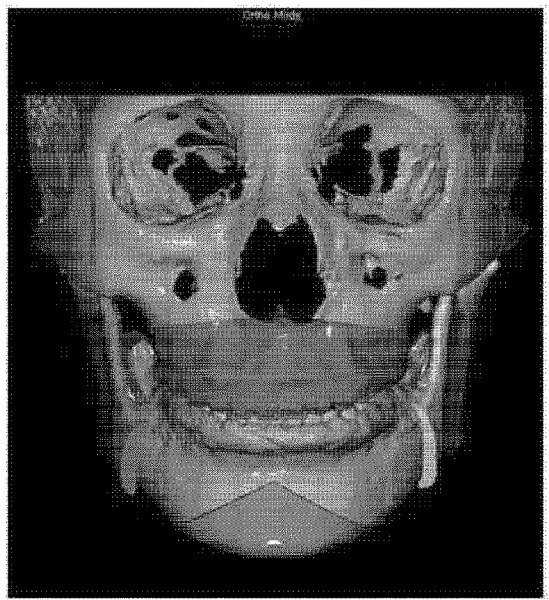
FIG. 9 shows the cut jaw bone pieces of FIG. 8 recombined via virtual orthognathic surgery.
Figure 9:
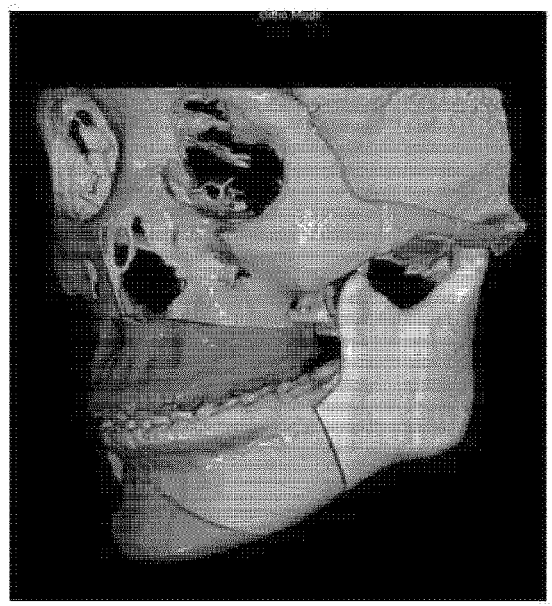

FIG. 9 shows the cut jaw bone pieces of FIG. 8 recombined via virtual orthognathic surgery, where drawing (A) shows a front view, and drawing (B) shows a side view.

Next, based on the result of the virtual orthognathic surgery received from the dental clinic server 103, the orthognathic device manufacturer server 104 designs an orthognathic assist device, which may be manufactured by a manufacturer technician and provided to the dental clinic (step S205). Here, the orthognathic assist device may be manufactured not only at the orthognathic device manufacturer but also at the dental clinic or a factory.

A step may further be included that involves the orthognathic device manufacturer server 104 verifying whether or not the result of the virtual orthognathic surgery is adequate by comparing the virtual orthognathic surgery result received from the dental clinic server 103 with the CT analysis data from before the orthognathic surgery.

Figure 10:
FIG. 10 shows comparison results between CT data from before and after virtual orthognathic surgery using an orthognathic system according to an embodiment of the present invention, in the form of a 2-dimensional image.
Figure 11:
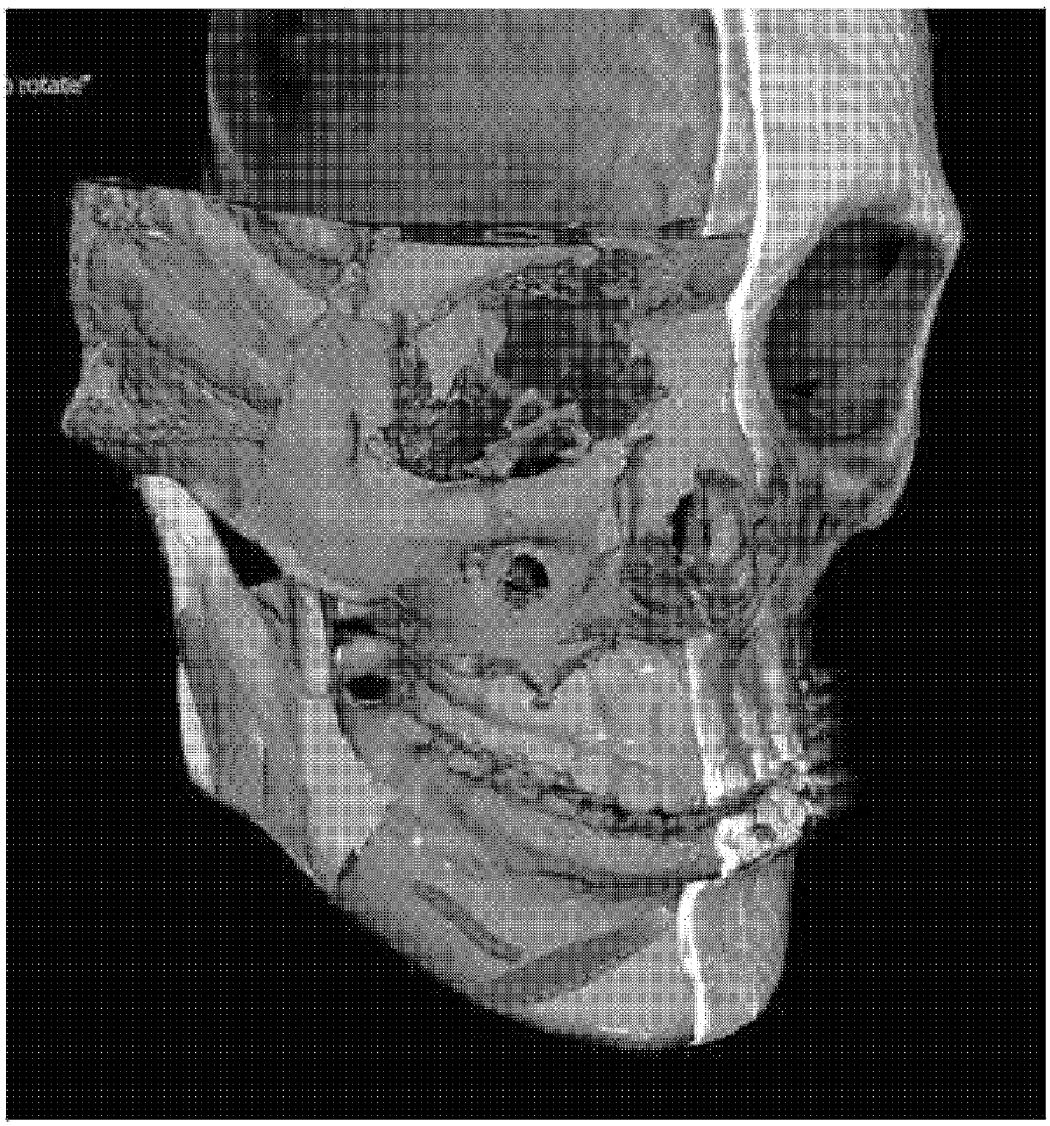
FIG. 11 shows comparison results between CT data from before and after virtual orthognathic surgery using an orthognathic system according to an embodiment of the present invention, in the form of a 3-dimensional image.

FIG. 10 and FIG. 11 show comparison results between CT data from before and after the virtual orthognathic surgery, FIG. 10 showing the results as a 2-dimensional image, and FIG. 11 showing the results as a 3-dimensional image.

Figure 12:
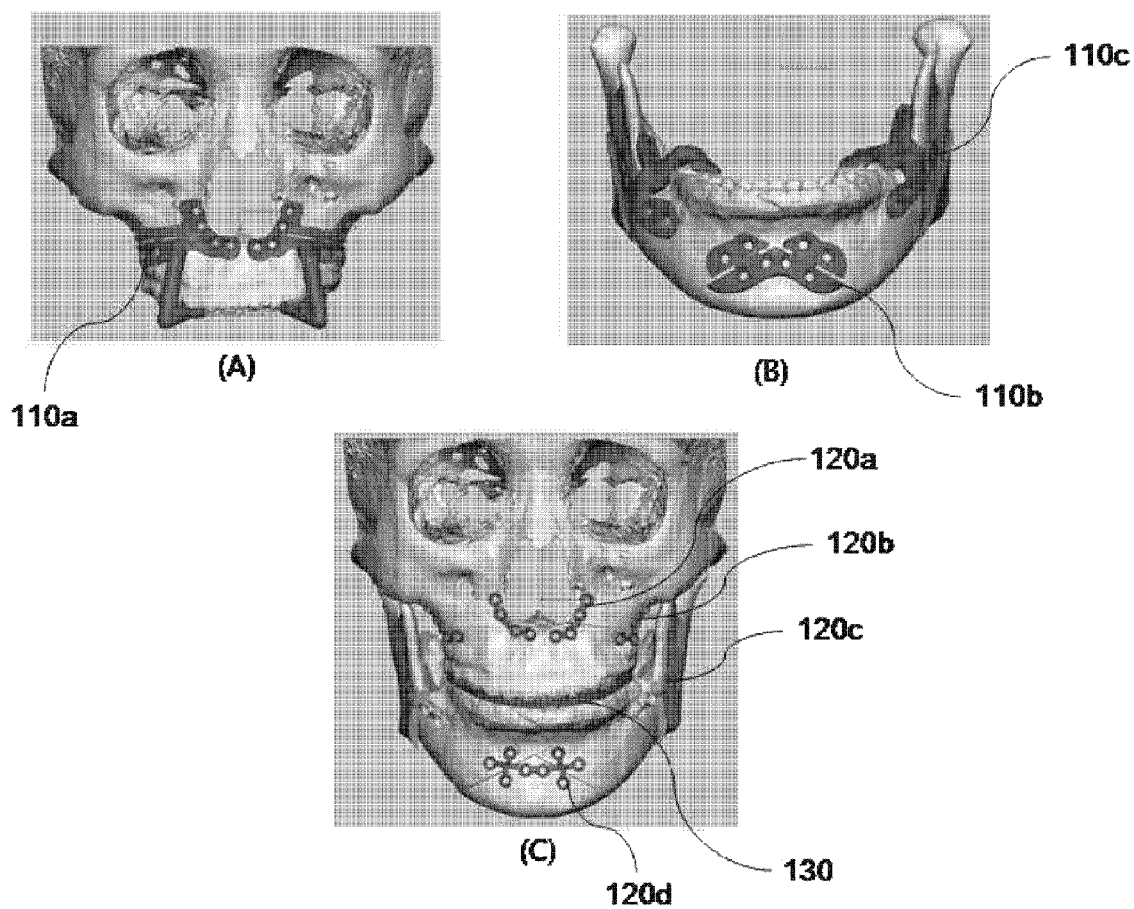
FIG. 12 shows sawing guides, jaw-bone fixation plates, and an arch fixation plate attached to the maxillary and mandibular bones as utilized in an orthognathic system according to an embodiment of the present invention.

Also, the orthognathic assist device manufactured by the orthognathic device manufacturer includes sawing guides 110a to 110c for cutting the jaw bones during actual orthognathic surgery, as illustrated in drawings (A) and (B) of FIG. 12, and fixation plates 120a-120d for guiding the positions of fixation pins that affix the jaw bones after parts of the jaw bones cut by way of the sawing guides 110a to 110c are moved by the virtual orthognathic surgery, as illustrated in drawing (C) of FIG. 12, as well as an arch fixation plate (intermittent stent) 130 serving as a temporary fixture clamped between the maxilla and the mandible for securing the maxillary arch and mandibular arch onto positions of the virtual orthognathic surgery when affixing the jaw-bone fixation plate 120a-120d.

Here, the sawing guides 110a to 110c may be manufactured by extracting the saw-blade guidance devices designed over the jaw bones into a file for processing and processing the extracted file with a 3D printer. Here, materials such as synthetic resin or specialized synthetic rubber may be used for the sawing guides.

The jaw-bone fixation plates 120a-120d may be manufactured by extracting the jaw-bone fixation plates designed over the jaw bones into a file for processing and processing the extracted file with a precision mill. While any material harmless to the human body may be used as the material for the jaw-bone fixation plates, a preferred embodiment may use titanium.

Figure 13:
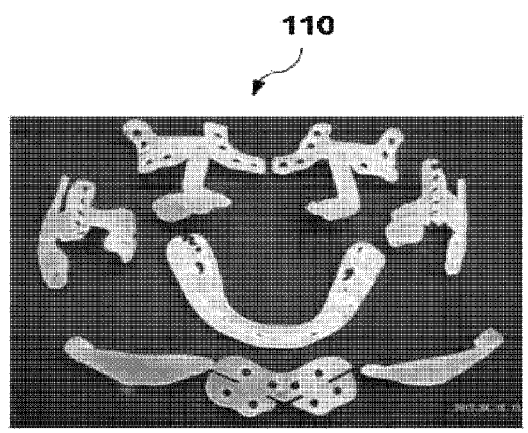
FIG. 13 shows sawing guides and jaw-bone fixation plates of various forms utilized in an orthognathic system according to an embodiment of the present invention.
Figure 13:
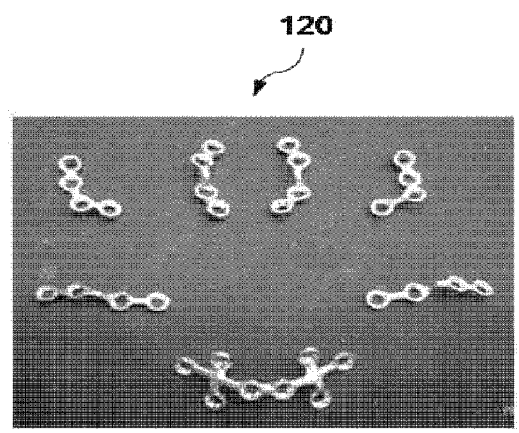

Lastly, a dentist performs actual orthognathic surgery by using the orthognathic assist device provided from the orthognathic device manufacturer (step S206). That is, a dentist at the dental clinic performs actual orthognathic surgery with the sawing guides 110 and jaw-bone fixation plates 120 of various forms, such as those illustrated in drawings (A) and (B) of FIG. 13, affixed by fixation pins (not shown) onto the corresponding positions of the maxilla and mandible, as in drawings (A), (B), and (C) of FIG. 12 described above. As the orthognathic surgery entails cutting the jaw bones with a surgical saw along the cutting lines directed by the sawing guides 110, the jaw bones may be cut as intended in a stable manner, and possible deviations of the saw blade during the orthognathic surgery due to negligence on the part of the orthognathic operator or due to some other unexpected causes may be prevented beforehand. Thus, the orthognathic surgery may be performed safely with minimal surgical side effects to the patient.

Also, by rejoining the separated jaw bones using the jaw-bone fixation plates 120, the jaw bones may be positioned and moved accurately to the positions designated before the orthognathic surgery, whereby the (bimaxillary) orthognathic surgery may be completed successfully.

The following provides further information on the series of procedures for cutting the jaw bones with a surgical saw along the cutting lines directed by the sawing guides 110 and rejoining the separated jaw bones using the jaw-bone fixation plates 120.

In one example, the positions of the bones to be removed are chosen by way of a simulation program, and the shape of the bones after the surgical procedure is matched virtually, after which the positions of the jaw-bone fixation plates 120 as well as the types of the jaw-bone fixation plates 120 are determined, and the positions of screw holes for affixing the jaw-bone fixation plates 120 are designated.

Afterwards, the lines along which to remove the bone are finalized, and the types and fixation positions of the sawing guides 110 for guiding the cutting are designated. Here, the positions of the screw holes for affixing the sawing guides 110 are designated in the same manner as that for the screw holes of the jaw-bone fixation plates 120.

During the surgical procedure, the bone is removed along the lines guided by the sawing guides 110 described above, and it is checked whether or not the pre-designated positions of the screw holes for the jaw-bone fixation plates 120 match those of the screw holes for the sawing guides 110. Here, if the positions of the screw holes for the jaw-bone fixation plates 120 do not match the positions of the screw holes for the sawing guides 110, this would mean that the bone removal was done improperly, and additional corrective actions may be performed accordingly. By performing the procedure as above, it is possible to verify whether the procedure was conducted successfully or not.

As set forth above, an orthognathic system using a 3-dimensional hybrid image constructing program according to an embodiment of the present invention performs virtual orthognathic surgery by using a 3-dimensional hybrid image constructing program and, based on the result of the virtual orthognathic surgery, designs and manufactures orthognathic assist devices needed for actual orthognathic surgery and provides the orthognathic assist devices to the orthognathic operator, so that the operator may perform orthognathic surgery safely and efficiently with minimal surgical side effects to the patient.

While the present invention is described above in detail with reference to certain preferred embodiments, the invention is not limited to the embodiments above. It should be apparent to those of ordinary skill in the art that various modifications and adaptations may be conceived without departing from the technical spirit of the present invention. Therefore, the true scope of protection of the present invention should be interpreted from the scope of claims below, and all technical features within the scope of equivalency are to be interpreted as being encompassed in the scope of the invention.

The invention claimed is:

1. An orthognathic system comprising:
a CT imaging apparatus configured to perform CT imaging of a skull of a patient receiving orthognathic surgery for orthognathic diagnosis planning;
a dental clinic server;
an orthognathic device manufacturer server; and
wherein the dental clinic server is configured to prepare preliminary data for orthognathic surgery based on CT image data acquired by the CT imaging apparatus, transmit the preliminary data to the orthognathic device manufacturer server, perform virtual orthognathic surgery by inputting osteotomy data received from the orthognathic device manufacturer server into a 3-dimensional hybrid image constructing program, and transmit a result of the virtual orthognathic surgery to the orthognathic device manufacturer server, and
wherein the orthognathic device manufacturer server is configured to merge CT data with gingival data based on the preliminary data received from the dental clinic server by using the 3-dimensional hybrid image constructing program, generate a jaw-bone 3-dimensional image file for virtual orthognathic surgery by extracting the merged data, cut a jaw bone within a program by using the generated jaw-bone 3-dimensional image file, and transmit data relevant to the osteotomy to the dental clinic server;

an orthognathic surgery module,
- wherein the orthognathic surgery module analyzes a jaw bone in a 3D model, presents an orthognathic surgery method suitable for the patient, cuts a necessary part in the 3D model accordingly, performs the virtual orthognathic surgery, and recreates a positional relationship of the jaw bone altered after the orthognathic surgery,
- wherein the orthognathic surgery module is configured to design a sawing guide having holes and needed for cutting the jaw bone and a fixation plate having holes and for affixing the jaw bone and accurately recreating the positional relationship, based on the recreated result,
- wherein the orthognathic surgery module is configured to design the sawing guide and the fixation plate such that at least one of the holes for affixing the sawing guide is formed in a same position of the jaw bone as at least one of the holes for affixing the fixation plate; and
- a dental implant module configured to implement an environment for implant diagnosis and virtual diagnosis by overlapping the CT image data of the patient with a 3D scanned image of an oral cavity or an oral-cavity model,
  - wherein the dental implant module is configured to choose an implanting position by merging an image of a repaired tooth onto data obtained after overlapping the CT image data and the scanned image of the oral cavity or the oral-cavity model, and the dental implant module is configured to determine an orthognathic surgery method and a drilling order for implanting by using a color bone quality analysis of an implanting site.

2. The orthognathic system according to claim 1, further comprising a scanner configured to scan an oral-cavity model fabricated by way of a dental impression taken from the patient receiving orthognathic surgery.

3. The orthognathic system according to claim 2, wherein the preliminary data prepared by the dental clinic server is obtained by incorporating oral-cavity model scan data into the CT image of the skull of the patient, the oral-cavity model scan data obtained by scanning the oral-cavity model.

4. The orthognathic system according to claim 1, wherein the orthognathic device manufacturer server is configured to perform surface treatment on 3-dimensional image data (image) for precise virtual orthognathic surgery prior to cutting the jaw bone in the program.

5. The orthognathic system according to claim 1, wherein the dental clinic server, in performing the virtual orthognathic surgery, moves and rotates jaw bone pieces cut into separate parts within the program to perform the virtual orthognathic surgery.

6. The orthognathic system according to claim 1, wherein the orthognathic device manufacturer server is further configured to compare a result of the virtual orthognathic surgery received from the dental clinic server with CT analysis data from before orthognathic surgery to verify a result of the virtual orthognathic surgery.

7. The orthognathic system according to claim 1, wherein the orthognathic device manufacturer server is further configured to design an orthognathic assist device based on a result of the virtual orthognathic surgery received from the dental clinic server.

8. The orthognathic system according to claim 7, wherein the orthognathic assist device comprises a sawing guide for cutting each jaw bone during actual orthognathic surgery, a jaw-bone fixation plate for guiding a position of a fixation pin configured to affix the jaw bone after each part of the jaw bone cut by way of the sawing guide is moved by the virtual orthognathic surgery, and an arch fixation plate serving as an intermittent stent clamped between a maxilla and mandible for securing a maxillary arch and mandibular arch to positions of the virtual orthognathic surgery when affixing the jaw-bone fixation plate.

* * * * *